US009894942B2

(12) United States Patent
Burrell

(10) Patent No.: US 9,894,942 B2
(45) Date of Patent: Feb. 20, 2018

(54) FUNNEL SUPPORT ACCESSORY FOR A BREAST PUMPING SYSTEM

(71) Applicant: PumpNDo, LLC, Hesperia, MI (US)

(72) Inventor: Julie Ann Burrell, Hesperia, MI (US)

(73) Assignee: PumpNDo, LLC, Hesperia, MI (US)

( * ) Notice: Subject to any disclaimer, the term of this patent is extended or adjusted under 35 U.S.C. 154(b) by 0 days.

(21) Appl. No.: 15/470,995

(22) Filed: Mar. 28, 2017

(65) Prior Publication Data

US 2017/0280787 A1    Oct. 5, 2017

Related U.S. Application Data

(60) Provisional application No. 62/314,454, filed on Mar. 29, 2016.

(51) Int. Cl.
*A41C 3/04* (2006.01)
*A61M 1/06* (2006.01)
*A41D 1/20* (2006.01)

(52) U.S. Cl.
CPC ............ *A41C 3/04* (2013.01); *A41D 1/205* (2013.01); *A61M 1/062* (2014.02); *A61M 2202/0014* (2013.01); *A61M 2202/04* (2013.01)

(58) Field of Classification Search
CPC .... A41C 3/04; A41C 3/08; A41D 1/20; A41D 1/205
USPC ............... 2/114, 104, 115, 69, 88, 49.1–49.4
See application file for complete search history.

(56) References Cited

U.S. PATENT DOCUMENTS

| 321,384 A * | 6/1885 | Presley | G09F 3/20 40/651 |
|---|---|---|---|
| 5,034,999 A * | 7/1991 | Lubbers | A41D 1/205 2/104 |
| 5,086,511 A * | 2/1992 | Kobayashi | H04B 1/16 455/156.1 |
| 5,848,439 A * | 12/1998 | Huseth | A41D 1/205 2/104 |
| 6,004,186 A * | 12/1999 | Penny | A61M 1/062 2/104 |
| 6,821,185 B1 * | 11/2004 | Francis | A41C 3/04 450/36 |
| 6,866,558 B2 * | 3/2005 | Luciano | A41C 3/04 450/36 |
| D523,212 S | 6/2006 | Iourina | |
| 7,611,399 B2 | 11/2009 | Brigham | |
| 7,811,248 B2 | 10/2010 | Bjorge | |

(Continued)

*Primary Examiner* — Gloria Hale
(74) *Attorney, Agent, or Firm* — Gardner, Linn, Burkhart & Flory, LLP

(57) ABSTRACT

A funnel support accessory attaches to a breastfeeding garment, such as a nursing bra, to support a funnel of a breast pumping system at a nipple area of the wearer's breast, so as to generally conceal the wearer's breasts and allow the wearer to perform other tasks while pumping in a hands-free manner. The funnel support accessory includes a fabric panel having at least one central opening configured to engage the funnel of the breast pumping system. The funnel support accessory also includes an engagement element disposed at an upper portion of the fabric panel to attach to an attachment feature of a breastfeeding garment. The fabric panel supports the engaged funnel of the breast pumping system generally over an exposed nipple area, such that the funnel seals against the nipple area without using a hand to support the funnel.

19 Claims, 12 Drawing Sheets

(56) References Cited

U.S. PATENT DOCUMENTS

| | | | |
|---|---|---|---|
| 8,192,247 B2* | 6/2012 | Abbaszadeh | A41C 3/04 2/104 |
| 8,323,070 B2* | 12/2012 | Abbaszadeh | A41C 3/04 2/104 |
| 9,155,339 B2 | 10/2015 | Alva | |
| 2003/0027491 A1* | 2/2003 | Cravaack | A41C 3/04 450/36 |
| 2003/0191427 A1 | 10/2003 | Jay et al. | |
| 2003/0199224 A1* | 10/2003 | Luciano | A41C 3/04 450/1 |
| 2008/0034462 A1* | 2/2008 | Ekelund | A41D 1/205 2/104 |
| 2008/0034463 A1* | 2/2008 | Ekelund | A41D 1/205 2/104 |
| 2008/0201817 A1* | 8/2008 | Ostrander | A41D 1/205 2/52 |
| 2010/0088800 A1* | 4/2010 | Pate-Gurule | A41D 1/205 2/104 |
| 2010/0159802 A1* | 6/2010 | Abbaszadeh | A41C 3/04 450/36 |
| 2010/0185144 A1 | 7/2010 | Bell | |
| 2013/0232661 A1* | 9/2013 | Huntley | A41C 3/08 2/104 |

* cited by examiner

FUNNEL SUPPORT ACCESSORY FOR A BREAST PUMPING SYSTEM

CROSS-REFERENCE TO RELATED APPLICATION

The present application claims the filing benefit of U.S. Provisional Application Ser. No. 62/314,454, filed Mar. 29, 2016, which is hereby incorporated herein by reference in its entirety.

FIELD OF THE INVENTION

The present invention relates generally to the field of breast pumping accessories, and more particularly to support accessories and devices for supporting breast pumping shields or cups or the like during use of a breast pump.

BACKGROUND OF THE INVENTION

It is common for women who are breastfeeding to express breast milk for the purpose of storing the milk to feed an infant at other times, such as when she is unable or unavailable to breast-feed the infant. Breast pumps are typically used to express the milk from a breast by generating intermittent suction or vacuum at a nipple to simulate a feeding or suckling infant. To provide the proper suction, breast pumps usually include a funnel or funnel-shaped cup or breast shield that is sized to be positioned over the nipple area of the breast. The breast pump then generates the intermittent suction in the funnel, such as via an electric motor or other vacuum device, to express the milk and draw it into a collection container attached to the funnel. However, to ensure that a seal is formed between the funnel and the breast for the intermittent suction to properly express milk, the woman typically holds the funnel tightly against the nipple area. This can be challenging when multi-tasking or pumping both breasts simultaneously.

SUMMARY OF THE PRESENT INVENTION

The present invention generally provides a funnel support accessory that attaches to a garment, such as a nursing bra or tank top, to support at least one funnel of a breast pumping system at a nipple area of the wearer's breast, so as to generally conceal the wearer's breasts and allow the wearer to perform other tasks while pumping in a hands-free manner. In accordance with one aspect of the present invention, a funnel support accessory for a breast pumping system includes a flexible panel, such as a fabric sheet, having at least one central opening configured to engage a funnel of the breast pumping system. The funnel support accessory also includes an engagement element disposed at an upper portion or area of the flexible panel. The engagement element of the funnel support accessory is configured to attach to an attachment feature of a breastfeeding garment, so as to allow the flexible panel to align the engaged funnel of the breast pumping system with a nipple area exposed by the breastfeeding garment. The funnel support accessory thereby supports the funnel in a sealed manner against the nipple area to allow the wearer to operate the pumping system without using a hand to support the funnel.

In accordance with another aspect of the present invention, a breastfeeding garment includes a flap portion that is configured to conceal a nipple area of a breast, where the flap portion is detachably secured at an attachment feature of the breastfeeding garment arranged above the nipple area of the wearer's breast. A funnel support accessory includes a fabric panel and a clip that is secured at an upper portion of the fabric panel. The fabric panel has a central opening that is configured to engage a stem portion of a funnel of a breast pumping system. Upon detaching the flap portion of the breastfeeding garment from the attachment feature, the flap portion is movable to expose the nipple area of the breast. After moving the flap portion to expose the nipple area, the clip of the funnel support accessory attaches to the attachment feature for supporting the funnel of the breast pumping system at the nipple area of the exposed breast.

Optionally, the funnel support accessory may include a pair of clips secured at spaced locations on the upper portion of the fabric panel, such that the clips each attach to a corresponding attachment feature at or near each breast. With such an arrangement, the fabric panel may provide two openings for supporting a funnel at each breast.

In accordance with yet another aspect of the present invention, a method of supporting a funnel of a breast pumping system includes detaching a flap portion of a breastfeeding garment from an attachment feature and moving the flap portion to expose a nipple area of the wearer's breast. An engagement element of a funnel support accessory is then attached to the attachment feature of the breastfeeding garment, where the engagement element is disposed at an upper portion of a fabric panel of the funnel support accessory, such that the fabric panel conceals the exposed breast. A funnel of the breast pumping system is engaged through a central opening in the fabric panel of the funnel support accessory to align the engaged funnel with the nipple area and support the funnel in a sealed manner against the nipple area, thereby allowing the wearer to operate the pumping system without using a hand to support the funnel.

These and other objects, advantages, purposes, and features of the present invention will become apparent upon review of the following specification in conjunction with the drawings.

DETAILED DESCRIPTION OF EMBODIMENTS

Figure 1:
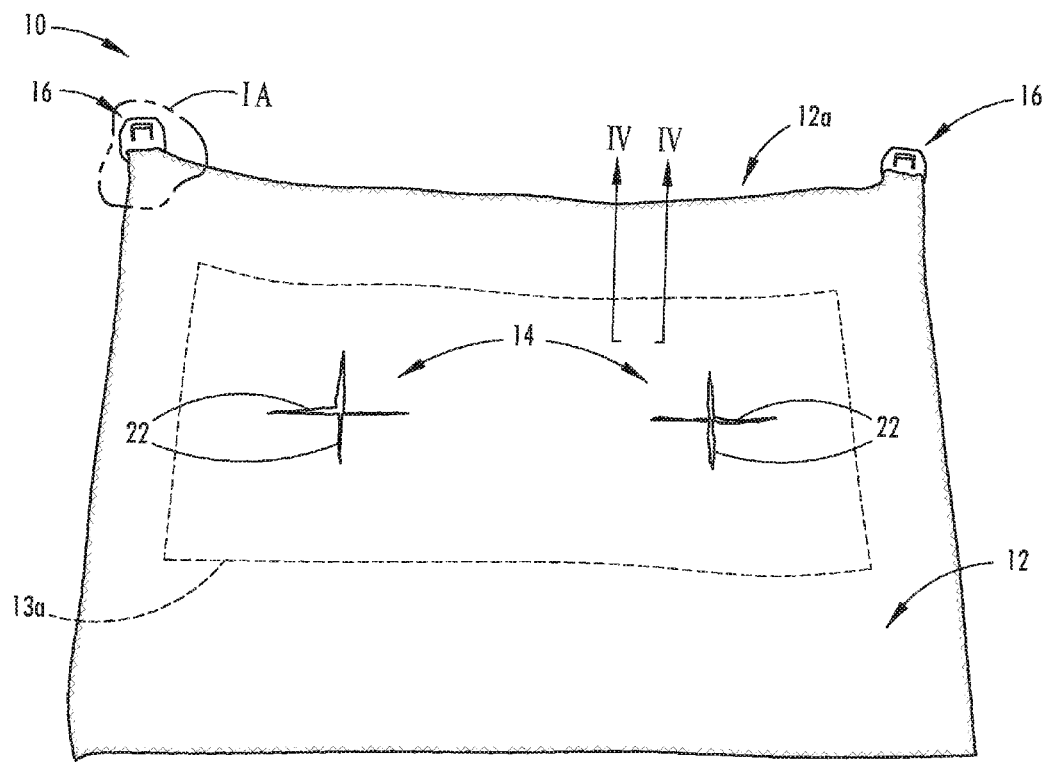
FIG. 1 is a front elevational view of a funnel support accessory, in accordance with the present invention.

Referring now to the drawings and the illustrative embodiments depicted therein, a funnel support accessory 10 attaches to a garment 40 (FIGS. 5-9), such as a nursing bra or tank top or other breastfeeding-configured garment, to support at least one funnel 60 of a breast pumping system at a nipple area of the wearer's breast, so as to generally conceal the wearer's breasts and allow the wearer to operate the breast pumping system without using a hand to support the funnel. The funnel support accessory 10 includes a flexible panel 12, such as a fabric sheet, having at least one central opening 14 configured to engage a funnel 60 of the breast pumping system. The funnel support accessory 10 also includes an engagement element 16 disposed at an upper portion of the flexible panel 12. The engagement element 16 is configured to attach to an attachment feature 42 of the garment 40, such as the nursing bra shown in FIG. 7, so as to allow the flexible panel 12 to support and generally locate the engaged funnel 60 of the breast pumping system at a nipple area exposed by the breastfeeding garment 40. The funnel support accessory 10 thereby supports the funnel 60 in a sealed manner against the nipple area to allow the wearer to perform other tasks while pumping in a hands-free manner.

Figure 3:
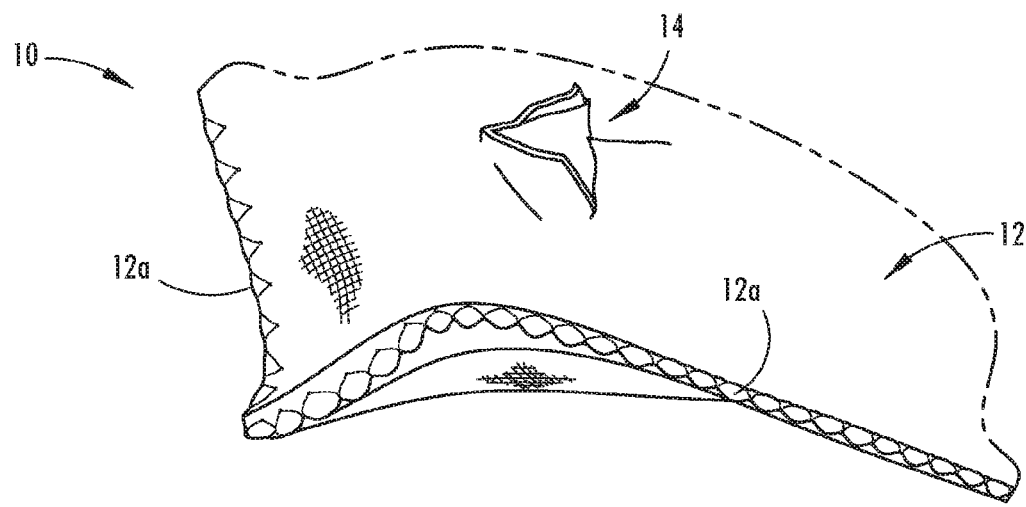
FIG. 3 is an elevational view of an edge of a fabric panel of the funnel support accessory shown in FIG. 1.
Figure 3A:
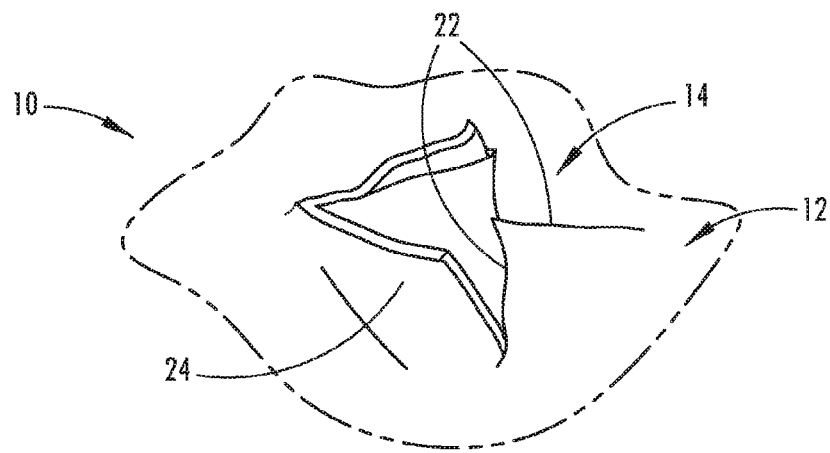
FIG. 3A is a perspective view of an opening in the fabric panel of the funnel support accessory shown in FIG. 1.

The flexible panel 12 is used to engage the funnel 60 and provide support between the funnel 60 and the engagement element 16 that attaches to the breast-feeding garment 40. Accordingly, the flexible panel 12 is typically configured with a material having sufficient thickness and rigidity to provide the funnel engagement and support functions, while also providing some flexibility, breathability, and a smooth surface for comfort against the skin of the wearer. The illustrated flexible panel 12 comprises two pieces of cotton flannel fused together with a fusible web 13 (FIG. 4), such as a hot melt adhesive or other fusible interfacing, and sewn at the outer edges 12a of the panel 12 with a serge stitch using a cotton thread to prevent the fabric from fraying. The fusible web 13 may be provided at a central region 13a (FIG. 1) of the flexible panel 12, such as to surround the central opening to provide a stiffened area of the flexible panel. Such a stiffened area of the flexible panel 12 may include at least two intersecting slits or cuts 22 that form wedge shaped flaps or corners 24 around the central opening 14 that are configured to support the funnel of the breast pumping system against the exposed breast. The stitches shown at the edges 12a (FIG. 3) are made in a zig-zag pattern, although other edge sealing stitches, covers, or sealing agents or techniques may be used to prevent fraying. It is also contemplated the flexible panel 12 may comprise a single sheet of woven fabric or various layers of fabrics or membranes or reinforcements or other materials, and may comprise various synthetic and natural woven fabric materials, including one or a blend of nylon, cotton, polyester, aramid, spandex, and the like, as well as other non-woven sheet material, such as leather, polymer, and the like.

Figure 2:
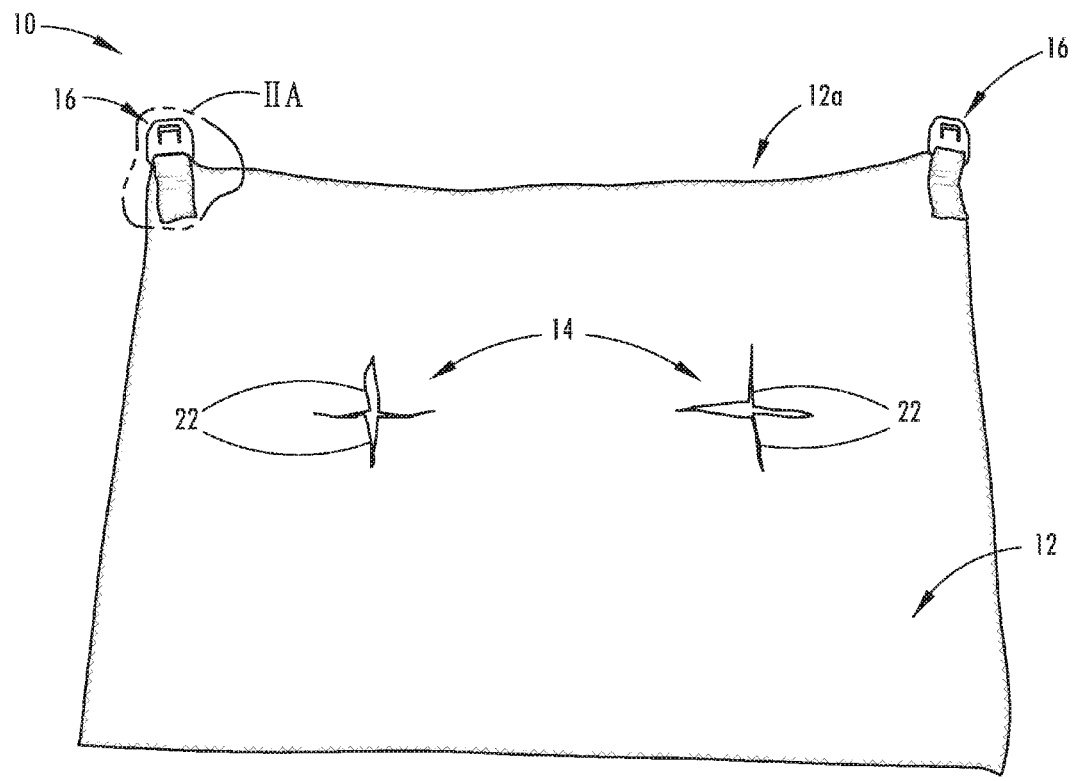
FIG. 2 is a rear elevational view of the funnel support accessory shown in FIG. 1.
Figure 10:
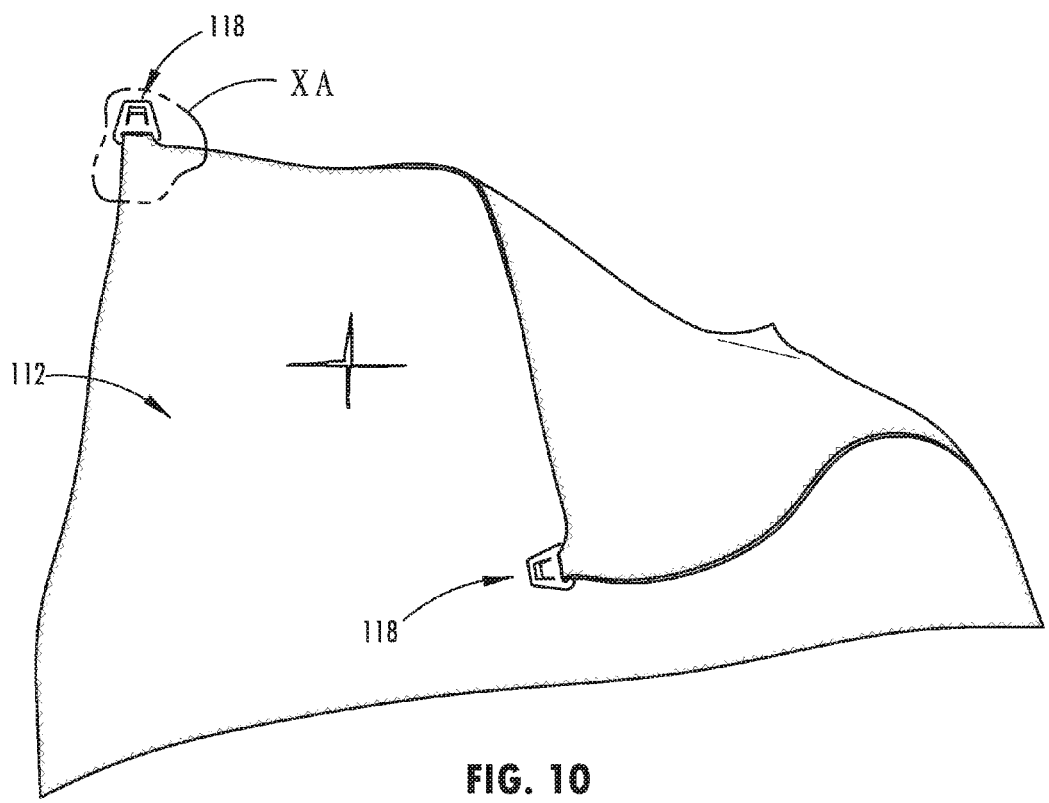
FIG. 10 is a rear perspective view of a funnel support accessory having an additional embodiment of an engagement element.
Figure 11:
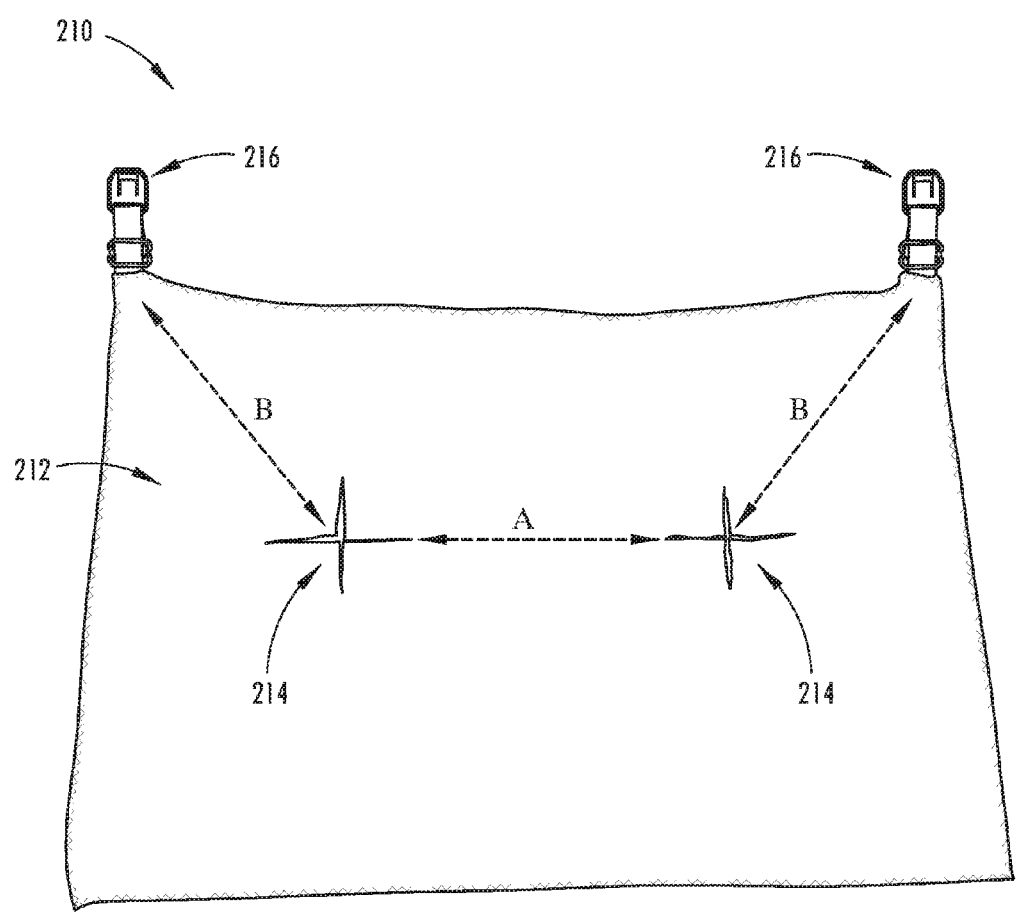
FIG. 11 is a front elevational view of a funnel support accessory having adjustability features.

As shown in FIGS. 1 and 2, the flexible panel 12 includes a substantially rectangular shaped sheet-like structure that is sized to span across a wearer's chest and cover both of the wearer's breasts, while providing two openings 14 at the central area of the panel 12 for supporting breast-pumping funnels 60. Although it is contemplated that the funnel support accessory can be configured to cover a single breast and support a single funnel at the covered breast, the illustrated funnel support accessory 10 provides coverage of both breasts and securely supports a funnel 60 at each breast, such that hands-free pumping at both breasts can be done simultaneously and/or pumping can be alternated between breasts without disengaging and reconfiguring the funnel and funnel support accessory. To provide appropriate coverage and support for different sized wearers, it is contemplated that different shaped or sized flexible panels may be used, such as a larger trapezoidal shape, as shown in FIG. 10, which can be sized for the lower portion corners to be tucked under a bra wire. Also, adjustability may be provided in different areas, such as illustrated by the support accessory 210 shown in FIG. 11 with desirable adjustment dimensions provided between the funnel support openings (dimension A) and/or between each funnel support opening the engagement elements (dimension B).

Figure 1A:
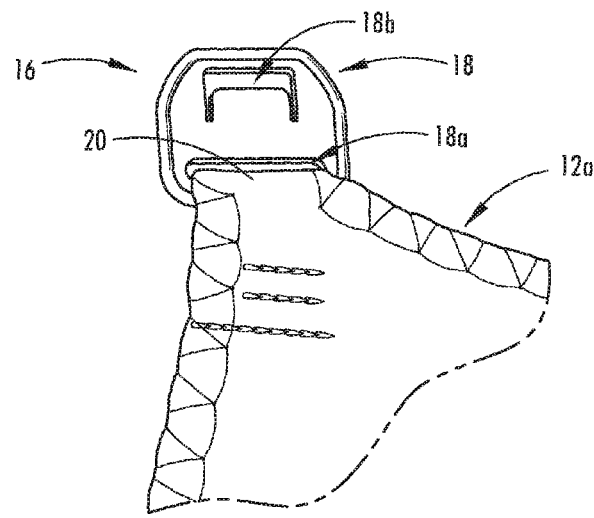
FIG. 1A is an enlarged view of an engagement element of the funnel support accessory shown in the area designated as section IA in FIG. 1.
Figure 2A:
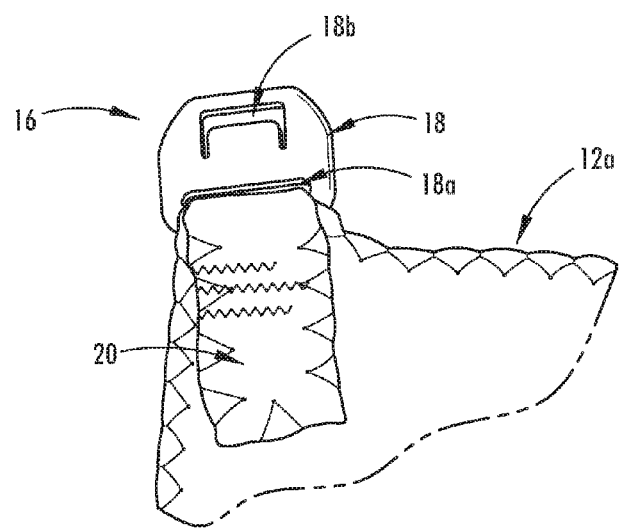
FIG. 2A is an enlarged view of the engagement element of the funnel support accessory shown in the area designated as section IIA in FIG. 2.
Figure 8:
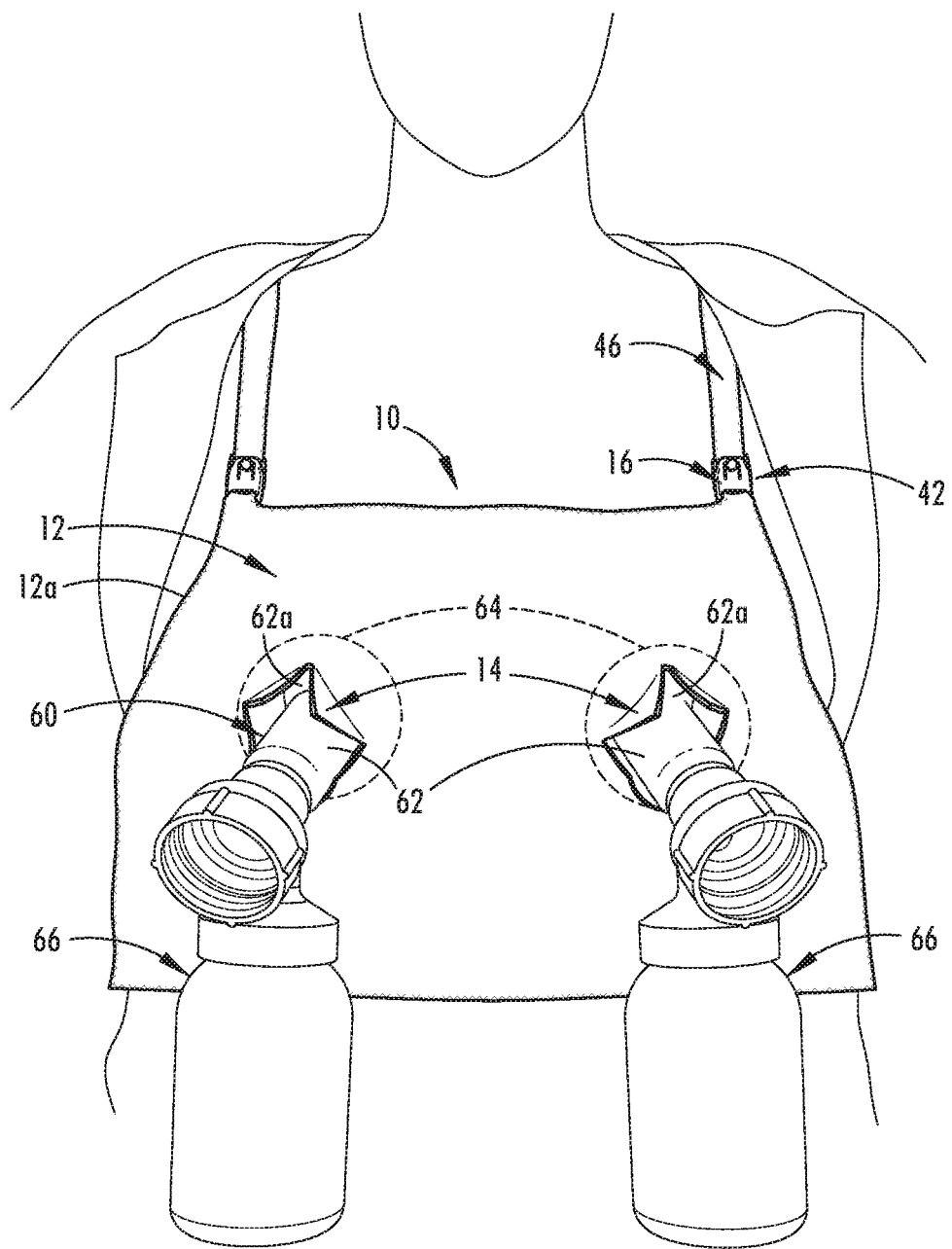
FIG. 8 is a front perspective view of the funnel support accessory attached to a nursing bra and supporting two funnels of a breast pumping system.
Figure 10A:
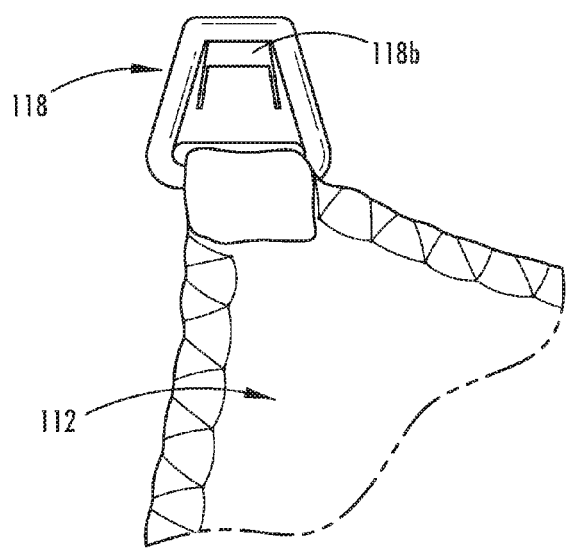
FIG. 10A is an enlarged view of the engagement element of the funnel support accessory shown in the area designated as section XA in FIG. 10.

The engagement elements 16 used to attach the funnel support accessory 10 to the breast-feeding garment 60 are secured to the upper portion of the flexible panel 12. The depicted funnel support accessory 10 has a pair of engagement elements 16 comprising clips secured at spaced locations on the upper edge of the fabric panel 12, such that the clips each attach to a corresponding attachment feature 42 at or near each breast (FIG. 8). As shown in FIGS. 1A and 2A, the engagement elements 16 each include a clip 18 and a strip or band of material 20, such as fabric or biased nylon tape, securing the clip 18 to the fabric panel 12. The illustrated clip 18 has a lower aperture 18a and an upper aperture 18b, although it is understood that the lower and upper apertures may optionally be formed as a single unitary aperture. The lower aperture 18a is attached to the flexible panel 12 with the strip of material 20 that is shown integrally extending from the flexible panel 12 through the lower aperture 18a. The strip of fabric 20 is then secured at the rear surface of the fabric panel 12 with additional stitching. It is contemplated that the clip 18 may be alternatively attached to the fabric panel 12, such as with a separate piece of material, adhesive, a mechanical fastener, such as a rivet, or the like. Furthermore, it is contemplated that an engagement element may be integrally formed with the flexible panel, such as by providing the flexible panel with an aperture for engaging an attachment feature of a breastfeeding garment. Another example of a clip 118 is shown in FIGS. 10 and 10A, attached to a different sized flexible panel 112. The clip 118 has a trapezoidal shape with the substantially liner sides that generally correlate with the shape of the upper aperture 118*b*.

Figure 4:
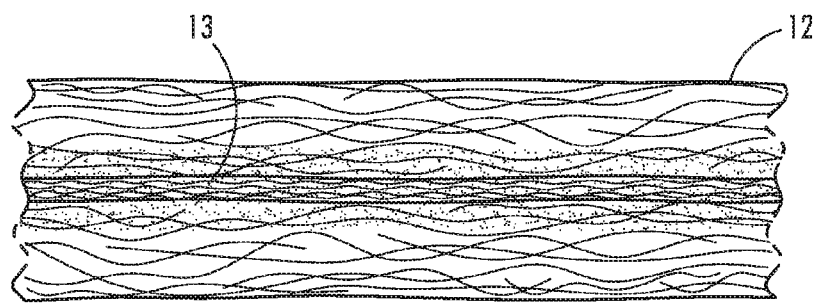
FIG. 4 is a cross-sectional view of the fabric panel, taken at line IV-IV shown in FIG. 1.

The openings 14 in the flexible panel 12 that are used to engage the shields or funnels 60 can be made any shape and size sufficient to allow a narrow stem portion 62 of the funnel 60 to extend through the flexible panel 12, while retaining a wide portion 64 of the funnel 60 at the rear surface of the fabric panel 12 (FIG. 8). The openings 14 formed in the flexible panel 12, as can be seen in FIGS. 1 and 2, are formed by two linear cuts 22 generally orthogonal to each other to form a plus shape, which preserves the majority of the fabric material surrounding the opening. As shown in FIG. 4, the opening 14 is expanded open to allow for insertion of the funnel by folding the flaps or corners 24 open away from the middle of the plus-shape formed by the linear cuts 22. Accordingly, the flaps or corners 24 of such a plus-shaped opening 14 may conceal portions of the nipple area that may be viewable through a translucent funnel, while also allowing different sized funnels, such as different diameter stem portions, to be retained by the opening 14.

Figure 5:
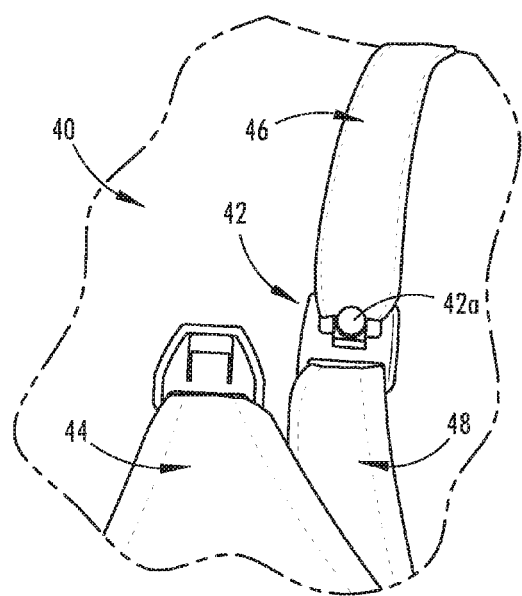
FIG. 5 is a perspective view of a flap portion of a breastfeeding garment being detached from an attachment feature on a shoulder strap.
Figure 6:
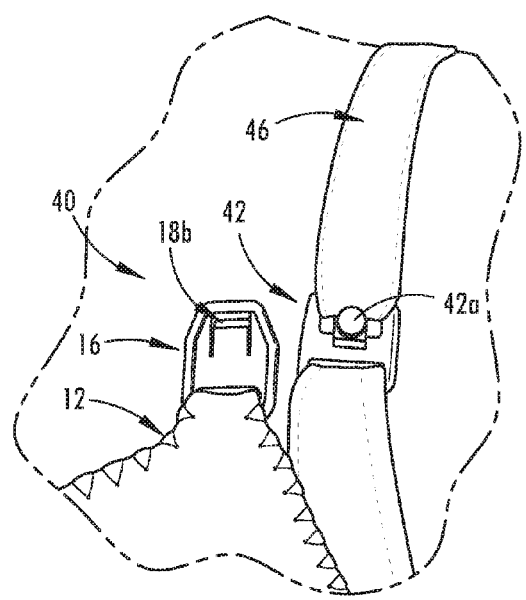
FIG. 6 is a perspective view of the engagement element of the funnel support accessory disengaged from the attachment feature on the shoulder strap.
Figure 7:
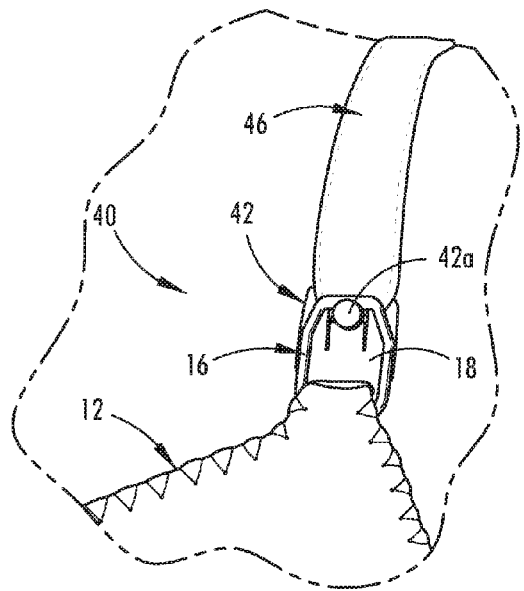
FIG. 7 is a perspective view of the engagement element of the funnel support accessory engaged with the attachment feature on the shoulder strap.

Referring now to FIGS. 5-7, a breastfeeding garment 40 may have a flap portion 44 that is configured to conceal a nipple area of a breast, such that the flap portion 44 is detachably secured at an attachment feature 42 of the breastfeeding garment 40 arranged above the nipple area of the wearer's breast. Specifically, the illustrated garment 40 is a nursing bra having a shoulder strap 46 supporting a breast cup section 48, where the attachment feature 42 for securing the flap portion 44 is located at a front section of the shoulder strap 46. Upon detaching the flap portion 44 from the attachment feature 42 (FIG. 5), the flap portion 44 is movable downward to expose the nipple area of the breast, as would be done for nursing an infant. After moving the flap portion 44 to expose the nipple area, the engagement element 16 of the funnel support accessory 10 attaches to the attachment feature 42 (FIG. 7) for supporting the flexible panel 12 in a desired position over the exposed breast. The illustrated attachment feature 42 includes a hook member 42*a* that protrudes away from the wearer and is arranged to receive the upper opening 18*b* on the clip 18 to provide vertical support to the flexible panel 12.

Figure 9:
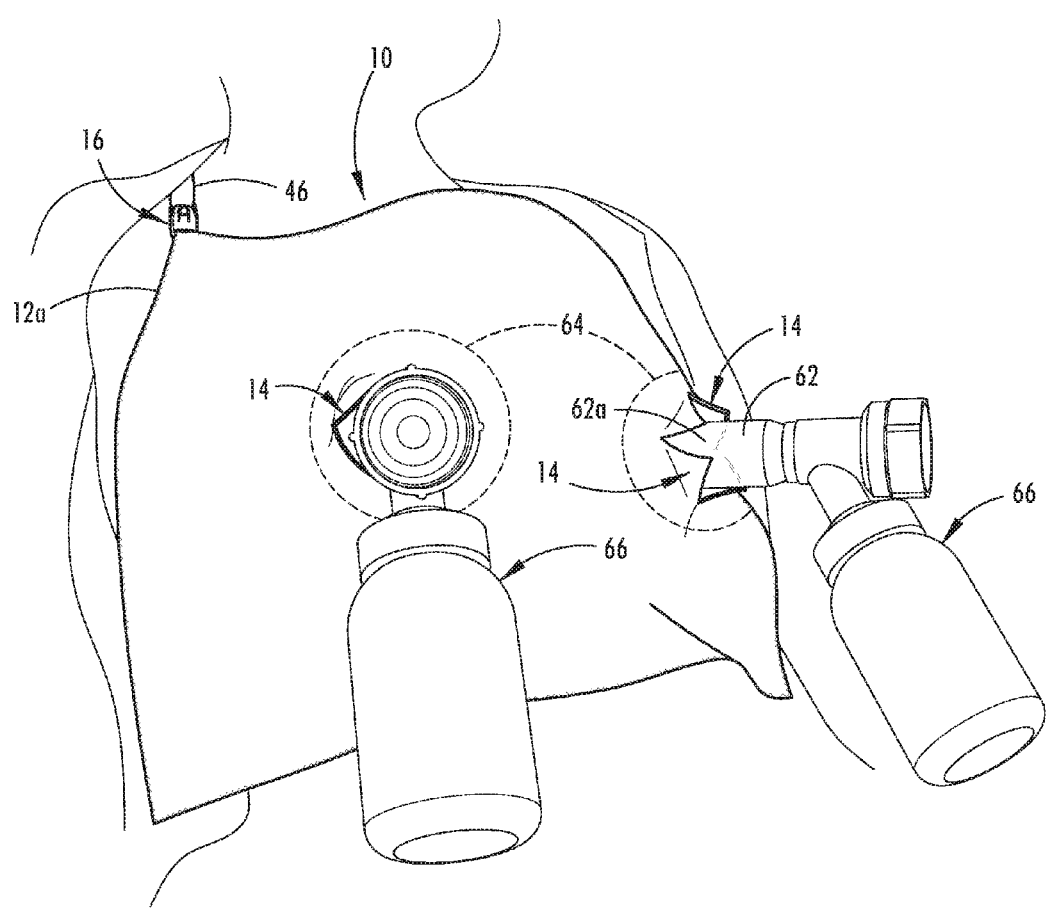
FIG. 9 is a lower side perspective view of the funnel support accessory shown in FIG. 8.

Upon attaching the engagement elements 16 of a funnel support accessory 10 to the attachment features 42 of the breastfeeding garment 40, the flexible panel 12 is positioned to align the openings 14 near or slightly above the nipple areas of each breast. The openings 14 may be positioned slightly higher than the nipples or nipple area, so as to accommodate raising the breast for pumping and/or shifting the opening down over the nipple when under the weight of the engaged funnel 60 and the suspended collection containers 66 (FIG. 9). The openings 14 may also be slightly off center, depending on the wearer's breast size. The flexible panel 12 loosely curves outward over the breasts to generally cover to wearer's breasts and provide comfortable support of the funnels 60 of the breast pumping system.

As shown in FIGS. 8 and 9, the funnels 60 of the breast pumping system are engaged through the central openings 14 in the fabric panel 12 to align the engaged funnels 60 with the nipple area of each breast and to support the funnel 60 in a sealed manner against each nipple area, thereby allowing the wearer to operate the breast pumping system without using a hand to support either funnel 60. Also, collection containers 66 of the breast pumping system are attached to the stem portions 62 of the funnels 60 and are supported by the funnel support accessory 10. Specifically, as shown in FIG. 9, the support accessory 10 is designed to support the free-hanging weight of the collection containers 66 by locating the engagement elements 16 above the nipple area of each breast. The heightened location of the engagement elements 16 thereby vertically support the weight at the upper section of the openings 14, which would otherwise cause the wide portions 64 of the funnels 60 to pull away from the breast. As such, with this design, an additional attachment at or below the nipple area, such as at the lower edge of the fabric panel, is generally unnecessary to provide support at the openings 14. However, it is contemplated that lower edge corners of the fabric panel may be tucked under the wearer's bra, such as under a lower support wire.

Figure 12:
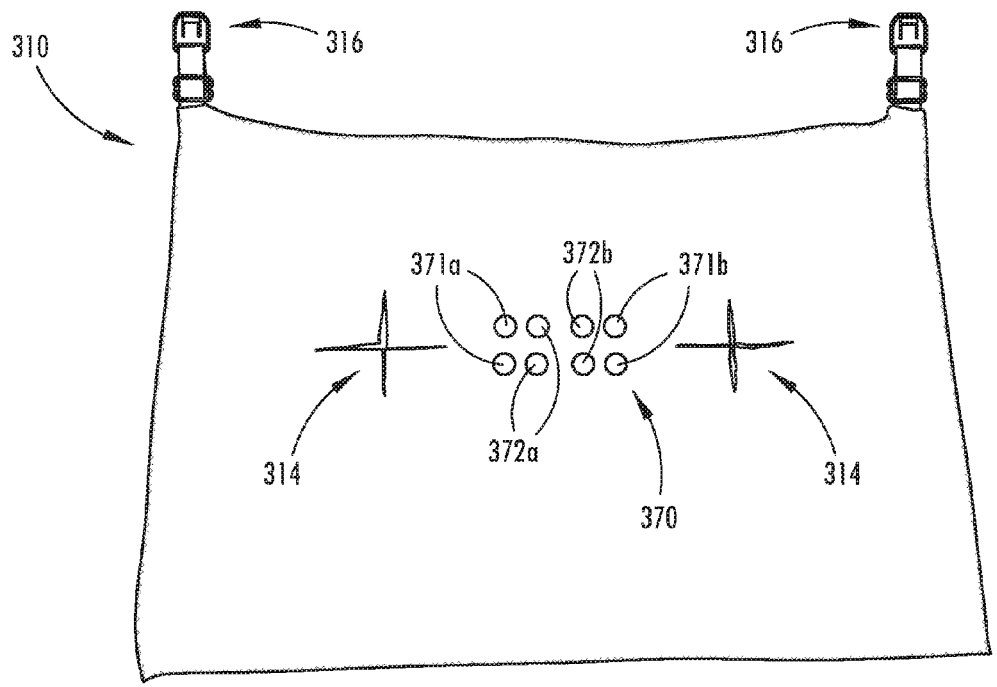
FIG. 12 is a front elevational view of a funnel support accessory having a width adjustment feature shown in an expanded condition.
Figure 12A:
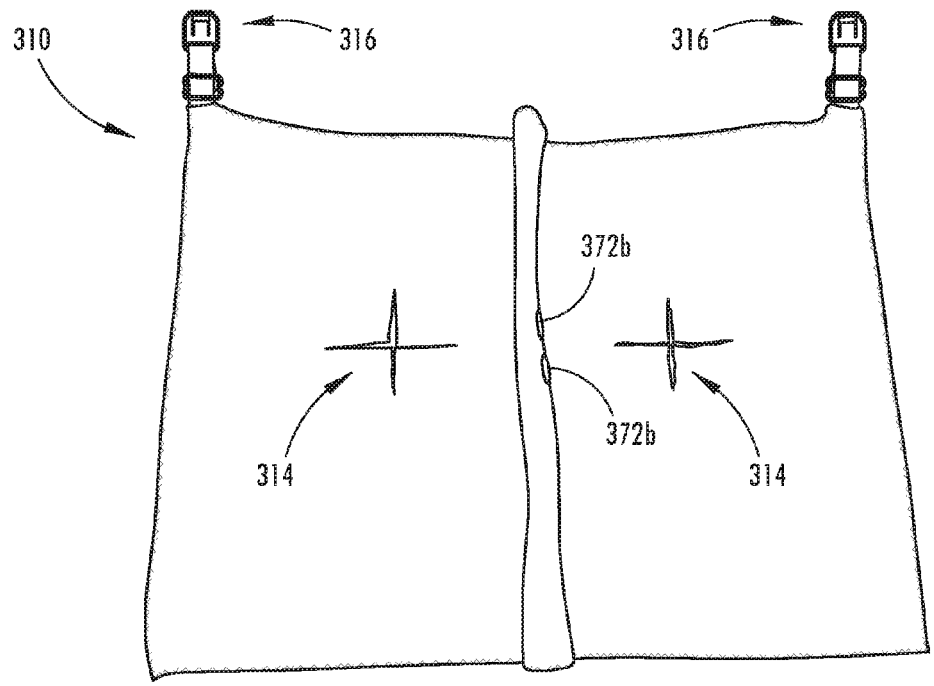
FIG. 12A is a front elevational view of the funnel support accessory shown in FIG. 12 with the width adjustment feature shown in an narrowed condition.

Referring now to FIGS. 11-14A, adjustable funnel support accessories 210, 310 are provided that allow the user to adjust different areas, such as to increase or decrease the width between the openings 214 (dimension A) or the generally vertical distance between the openings 214 and the engagement elements 216 (dimension B). As shown in FIGS. 12 and 12A, the dimension A may be adjustable with a width adjustment feature 370 that gathers and holds a select amount of material between the openings 314 to provide a desired width between the openings 314. The illustrated width adjustment feature 370 has four series of buttons, such as a snap-together buttons, arranged with columns of two, thus totaling eight buttons. However more or few buttons may be utilized in other embodiments to provide the desire about of the adjustability. The outermost buttons 371*a*, 371*b* may be attached together, such as shown in FIG. 12B, to reduce the width between the openings to the greatest extent. Similarly, the innermost buttons 372*a*, 372*b* may be attached together to reduce the width to an intermediate width that is greater than the width after attachment of the outermost buttons 371*a*, 371*b*.

Figure 13:
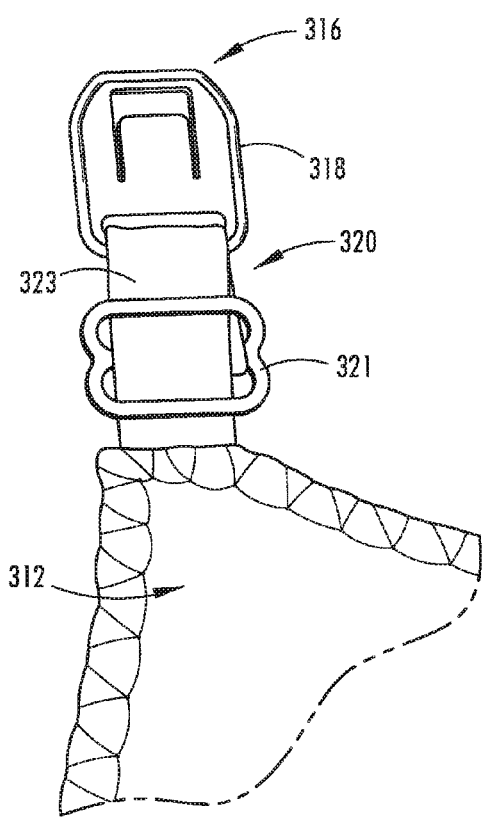
FIG. 13 is a front perspective view of a height adjustable feature of a funnel support accessory, shown in a shortened condition.
Figure 13A:
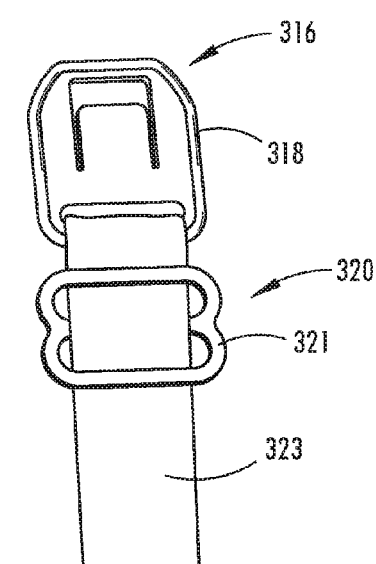
FIG. 13A is a front perspective view of the height adjustable feature shown in FIG. 13, shown in an elongated condition.
Figure 13A:
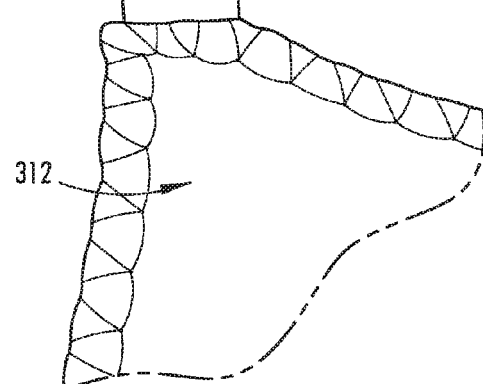
Figure 14:
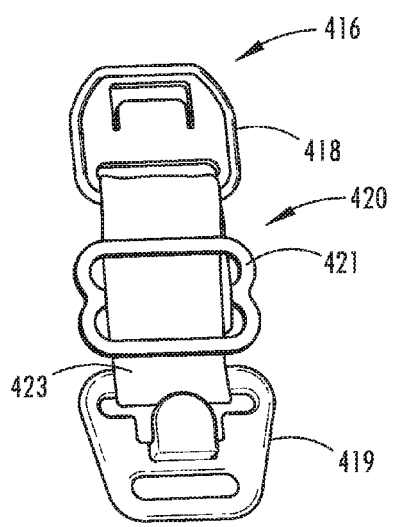
FIG. 14 is a front perspective view of a detachable height adjustable feature of a funnel support accessory, shown in a shortened condition.
Figure 14:
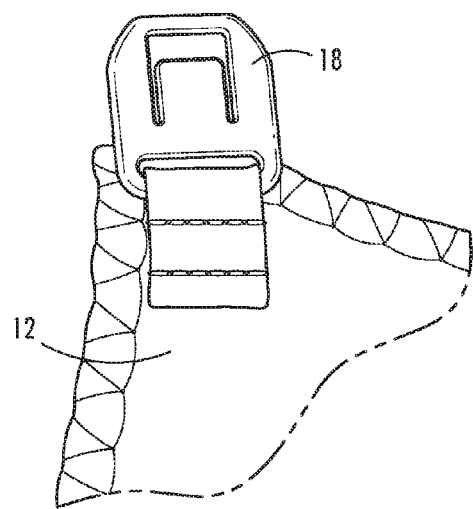
Figure 14A:
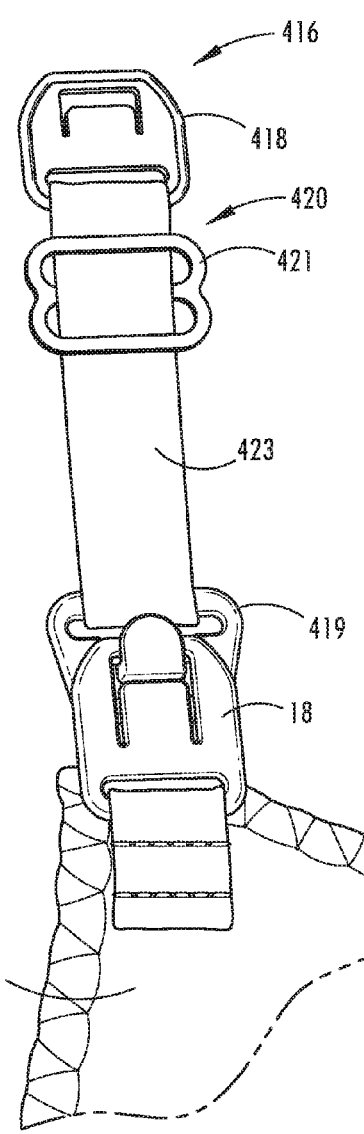
FIG. 14A is a front perspective view of the detachable height adjustable feature shown in FIG. 14, shown in an elongated condition.

With respect to adjustability of dimension B (FIG. 11), the funnel support accessory 310 may include an engagement element 316 that has an adjustable strap or band of material 320 that attaches between the clip 318 and the upper edge of the fabric panel 312. The adjustable strap 320 includes a slidable buckles 321 that are configured, like bra strap buckles, to move on a fabric strap 323 in a manner that adjusts the length of the adjustable strap 320 between a shortened length, as shown in FIG. 13) and an extended length, as shown in FIG. 13A. It is contemplated that the adjustable strap 320 may optionally include alternative features or arrangements to adjust the length to provide that adjustability of dimension B. Furthermore, as shown in FIGS. 14-14A, a detachable version of an engagement element 416 that has an adjustable strap or band of material 420 that attaches between the clip 418 at the upper end and an intermediate connector 419 at the lower end. The detachable engagement element 416 may then adapt the funnel support accessory 10 shown in FIG. 1 by attaching the intermediate connector 419 to the clip 18 at the upper edge of the fabric panel 12. The adjustable strap 420 similarly includes a slidable buckles 421 that are configured to move on a fabric strap 423 in a manner that adjusts the length of the adjustable strap 420.

Figure 15:
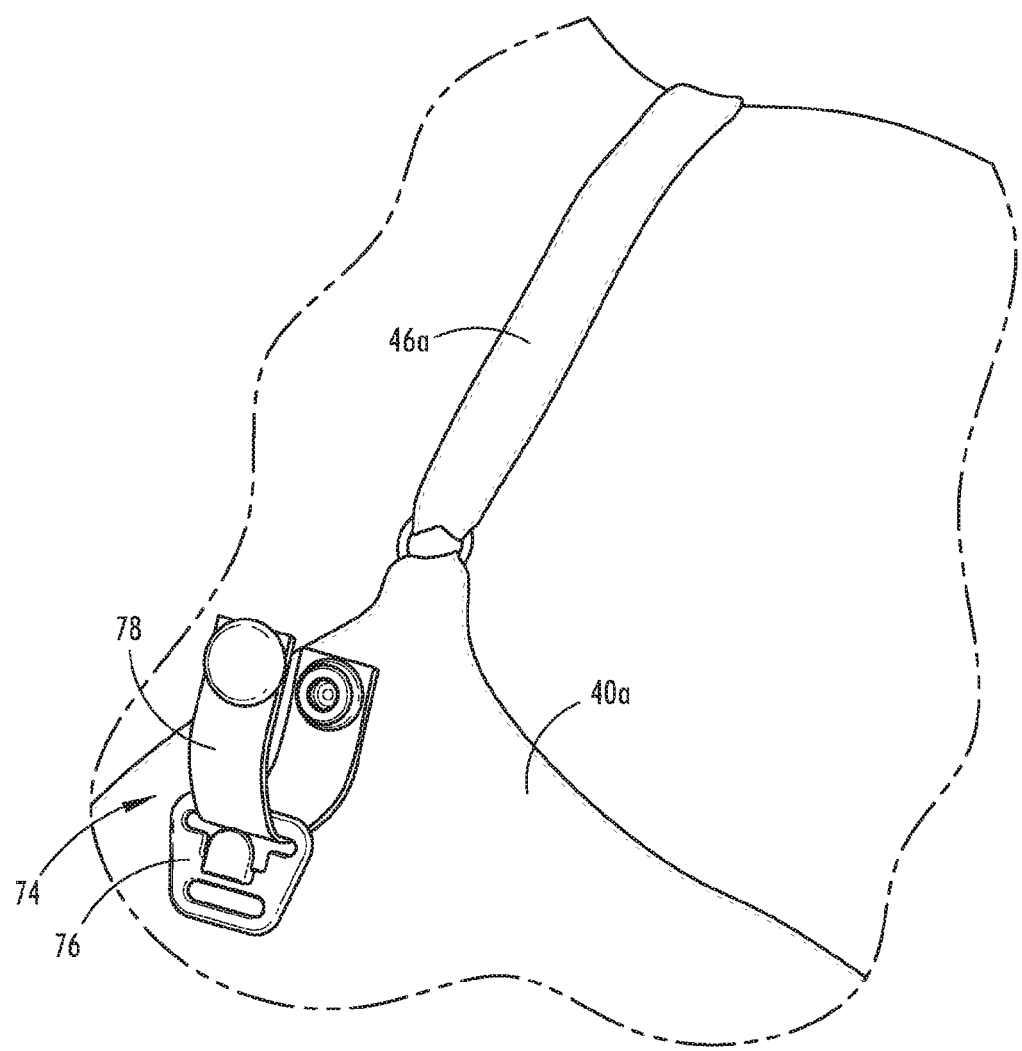
FIG. 15 is an attachment feature that can attach to a standard bra strap for engaging the engagement element of a funnel support accessory.

In addition to supporting the funnels 60 in the desired position, the fabric panel 12 also generally covers and conceals the wearer's breasts. The funnel support accessory 10 supports the wide portion 64 of the funnels 60 in a sealed manner against the nipple areas to allow the wearer to perform other tasks while pumping in a hands-free manner. The funnel support accessory 10 thereby also allows the user to then utilize a nursing bra or tank top that could be desirable for nursing an infant prior to attaching the funnel support accessory 10 and breast pumping system, such as to quickly and easily hold and care for the infant while breast pumping, as may be desired for mothers weaning an infant from breast milk or breast pumping to reduce swelling or mastitis symptoms. Another benefit of the funnel support accessory 10 is the convenience of it attaching to a woman's bra or tank top, eliminating the need to disrobe to put on a separate item that is exclusively used for breast pumping. Optionally, the user may utilize a standard bra 40a, such as shown in FIG. 15, and attach a modifiable connector 74 that includes an engagement element 76 to allow the standard bra 40a to accommodate and attach a funnel support accessory. The modifiable connector may include a button strap 78 that attaches around a bra strap 46a above the cup of a bra, such that the engagement element 76 is positioned approximately in the location of a nursing bra, so as to engage and support a funnel support accessory.

The disclosure has been described in an illustrative manner, and it is to be understood that the terminology, which has been used, is intended to be in the nature of words of description rather than of limitation. Many modifications and variations of the present disclosure are possible in light of the above teachings, and the disclosure may be practiced otherwise than as specifically described.

For purposes of this disclosure, the terms "upper," "lower," "right," "left," "rear," "front," "vertical," "horizontal," and derivatives thereof shall relate to the invention as oriented in FIG. 1. However, it is to be understood that the invention may assume various alternative orientations, except where expressly specified to the contrary. It is also to be understood that the specific devices and processes illustrated in the attached drawings, and described in this specification are simply exemplary embodiments of the inventive concepts defined in the appended claims. Hence, specific dimensions and other physical characteristics relating to the embodiments disclosed herein are not to be considered as limiting, unless the claims expressly state otherwise.

Changes and modifications in the specifically described embodiments may be carried out without departing from the principles of the present invention, which is intended to be limited only by the scope of the appended claims as interpreted according to the principles of patent law including the doctrine of equivalents.

The invention claimed is:

1. A combination of a breastfeeding garment and funnel support accessory for a breast pumping system, said combination comprising:
   a breastfeeding garment having a flap portion configured to conceal a nipple area of a breast of a wearer, wherein the flap portion is detachably secured at an attachment feature of the breastfeeding garment arranged above the nipple area of the breast;
   a funnel support accessory comprising a flexible panel and a clip secured at an upper portion of the flexible panel, wherein the flexible panel includes an opening configured to engage a stem portion of a funnel of the breast pumping system;
   wherein upon detaching the flap portion of the breastfeeding garment from the attachment feature, the flap portion is configured to move to expose the nipple area of the breast; and
   wherein upon moving the flap portion to expose the nipple area, the clip of the funnel support accessory attaches to the attachment feature for supporting the funnel support accessory at the breastfeeding garment; and
   wherein, with the funnel support accessory attached at the breastfeeding garment, the opening in the flexible panel is configured to support a funnel of the breast pumping system at the nipple area of the exposed breast of the wearer.

2. The combination of claim 1, wherein the breastfeeding garment comprises a shoulder strap supporting a breast cup section, and wherein the attachment feature is configured to secure the flap portion at a front section of the shoulder strap.

3. The combination of claim 2, wherein the breastfeeding garment comprises one of a nursing bra and a nursing tank top.

4. The combination of claim 1, wherein the flexible panel includes a fabric sheet, and wherein the clip and a second clip of the funnel support accessory are secured at spaced locations on the upper portion of the flexible panel and are configured to engage corresponding attachment features at or near each breast of the wearer.

5. The combination of claim 1, wherein the flexible panel includes two fabric sheets fused together via an adhesive at a region surrounding the opening to provide a stiffened area of the flexible panel.

6. The combination of claim 5, wherein the stiffened area of the flexible panel includes at least two intersecting slits that form wedge shaped flaps around the opening, and wherein the wedge shaped flaps are configured to support the funnel of the breast pumping system against the exposed breast.

7. The combination of claim 1, wherein an adjustable strap is attached between the clip and the upper portion of the flexible panel to provide vertical adjustment of the opening relative to the exposed breast.

8. The combination of claim 1, wherein an adjustment feature is disposed at the flexible panel between the opening and a second opening in the flexible panel to provide width adjustment of the flexible panel between the two openings.

9. A funnel support accessory for a breast pumping system, said funnel support accessory comprising:
   a fabric panel having at least one opening configured to engage a funnel of the breast pumping system;
   an engagement element disposed at an upper portion of the fabric panel;
   wherein the engagement element of the funnel support accessory is configured to engage an attachment feature of a breastfeeding garment to support the fabric panel at the breastfeeding garment; and
   wherein, when the fabric panel is supported at the breastfeeding garment and a funnel is engaged with the fabric panel, the opening of the fabric panel is configured to align the engaged funnel of the breast pumping system with a nipple area of a wearer exposed by the breastfeeding garment, thereby supporting the funnel against the nipple area.

10. The funnel support accessory of claim 9, wherein the engagement element is configured to engage to the attachment feature of the breastfeeding garment when a flap portion of a breastfeeding garment is detached from the attachment feature and moved to expose the nipple area of the wearer's breast.

11. The funnel support accessory of claim 10, wherein the fabric panel is configured to conceal a remaining portion of the nipple area and a corresponding breast of the wearer exposed by the flap portion and not exposed by the opening.

12. The funnel support accessory of claim 9, wherein the engagement element is configured to engage a breastfeeding garment comprising a nursing bra having the attachment feature disposed at a front section of a shoulder strap of the nursing bra.

13. The funnel support accessory of claim 9, further comprising a second clip secured at a spaced location on the upper portion of the fabric panel from the clip, such that the clips are each configured to engage a corresponding attachment feature at or near each breast of the wearer, such that the fabric panel is configured to span over each breast of the wearer.

14. The funnel support accessory of claim 9, wherein the fabric panel includes two fabric sheets fused together via an adhesive at a region surrounding the opening to provide a stiffened area of the fabric panel.

15. The funnel support accessory of claim 14, wherein the stiffened area of the fabric panel includes at least two intersecting slits that form wedge shaped flaps around the opening, and wherein the wedge shaped flaps are configured to support the funnel of the breast pumping system against the exposed breast of the wearer.

16. The funnel support accessory of claim 9, further comprising an adjustable strap that is attached between the engagement element and the upper portion of the fabric panel, and wherein the adjustable strap is configured to have an adjustable length that vertically adjusts the at least one opening relative to the exposed breast of the wearer.

17. The funnel support accessory of claim 9, wherein a width adjustment feature is disposed at the fabric panel between the opening and a second opening in the fabric panel to provide width adjustment between the two openings.

18. The funnel support accessory of claim 9, wherein, when the fabric panel is supported at the breastfeeding garment without the funnel engaged with the opening, the opening in the fabric panel is configured to be positioned at a raised location at or slightly above the nipple area, and wherein, when the funnel is engaged with the opening and the exposed breast of wearer is engaged in the funnel, the opening is configured for the weight of the engaged breast to move the opening downward to a desired location generally aligned with the nipple area.

19. A method of supporting a funnel of a breast pumping system, said method comprising:

having a wearer wearing a breastfeeding garment;

detaching a flap portion of the breastfeeding garment from an attachment feature of the breastfeeding garment;

moving the flap portion to expose a nipple area of a breast of the wearer;

attaching an engagement element of a funnel support accessory to the attachment feature of the breastfeeding garment, wherein the engagement element is disposed at an upper portion of a fabric panel of the funnel support accessory; and engaging a funnel of the breast pumping system through an opening in the fabric panel of the funnel support accessory to align the engaged funnel with the nipple area and support the funnel against the nipple area, thereby allowing the wearer to operate the pumping system without using a hand to support the funnel.

* * * * *